(12) United States Patent
DeJesus et al.

(10) Patent No.: US 11,970,635 B2
(45) Date of Patent: Apr. 30, 2024

(54) HOT MELT ADHESIVES AND USES THEREOF

(71) Applicant: HENKEL AG & CO., KGaA, Duesseldorf (DE)

(72) Inventors: Maria Cristina Barbosa DeJesus, Basking Ridge, NJ (US); Charles W. Paul, Madison, NJ (US); Valerie Alexis, Edison, NJ (US); Geetanjaliben Shah, Somerset, NJ (US)

(73) Assignee: HENKEL AG & CO. KGaA, Duesseldorf (DE)

( * ) Notice: Subject to any disclaimer, the term of this patent is extended or adjusted under 35 U.S.C. 154(b) by 0 days.

(21) Appl. No.: 18/047,380

(22) Filed: Oct. 18, 2022

(65) Prior Publication Data

US 2023/0066070 A1    Mar. 2, 2023

Related U.S. Application Data

(63) Continuation of application No. 15/784,576, filed on Oct. 16, 2017, now abandoned, which is a continuation of application No. PCT/US2016/023864, filed on Mar. 24, 2016.

(60) Provisional application No. 62/148,951, filed on Apr. 17, 2015.

(51) Int. Cl.
| | |
|---|---|
| *C09J 123/12* | (2006.01) |
| *A61L 15/24* | (2006.01) |
| *A61L 15/58* | (2006.01) |
| *A61L 31/04* | (2006.01) |
| *B32B 5/02* | (2006.01) |
| *B32B 7/12* | (2006.01) |
| *B32B 27/32* | (2006.01) |
| *C08L 23/08* | (2006.01) |
| *C08L 51/06* | (2006.01) |
| *C09J 7/21* | (2018.01) |
| *C09J 7/24* | (2018.01) |
| *C09J 7/35* | (2018.01) |
| *C09J 123/10* | (2006.01) |
| *C09J 123/14* | (2006.01) |

(52) U.S. Cl.
CPC ............ *C09J 123/12* (2013.01); *A61L 15/24* (2013.01); *A61L 15/58* (2013.01); *A61L 31/048* (2013.01); *B32B 5/022* (2013.01); *B32B 7/12* (2013.01); *B32B 27/32* (2013.01); *C08L 23/0869* (2013.01); *C08L 51/06* (2013.01); *C09J 7/21* (2018.01); *C09J 7/241* (2018.01); *C09J 7/35* (2018.01); *C09J 123/10* (2013.01); *C09J 123/14* (2013.01); *B32B 2307/51* (2013.01); *B32B 2535/00* (2013.01); *B32B 2555/02* (2013.01); *C09J 2423/006* (2013.01); *C09J 2423/10* (2013.01)

(58) Field of Classification Search
CPC ..... Y10T 428/249982; Y10T 428/2852; Y10T 442/2738; Y10T 442/2746; Y10T 442/2754; B32B 37/12; B32B 37/1207; B32B 37/1215; B32B 7/12; B32B 2307/1215; C09J 123/14; C09J 123/142; C09J 123/145; C09J 123/147; C09J 2423/10; A61F 2013/53908; C08L 23/10; C08L 23/142
USPC ......................................................... 442/150
See application file for complete search history.

(56) References Cited

U.S. PATENT DOCUMENTS

| | | | |
|---|---|---|---|
| 4,233,432 | A | 11/1980 | Curtis, Jr. |
| 5,171,628 | A | 12/1992 | Arvedson et al. |
| 5,256,717 | A | 10/1993 | Stauffer et al. |
| 5,331,033 | A | 7/1994 | Stauffer et al. |
| 5,397,843 | A | 3/1995 | Lakshmanan et al. |
| 6,120,487 | A | 9/2000 | Ashton |
| 6,143,818 | A | 11/2000 | Wang et al. |
| 6,218,457 | B1 | 4/2001 | Fralich et al. |
| 6,329,468 | B1 † | 12/2001 | Wang |
| 6,653,385 | B2 | 11/2003 | Wang et al. |
| 6,774,069 | B2 | 8/2004 | Zhou et al. |
| 6,833,404 | B2 | 12/2004 | Quinn et al. |
| 7,067,585 | B2 | 6/2006 | Wang et al. |
| 7,256,236 | B1 | 8/2007 | Hacker |
| 7,262,251 | B2 | 8/2007 | Kanderski et al. |
| 7,989,543 | B2 | 8/2011 | Karjala et al. |
| 8,394,879 | B1 | 3/2013 | Bradshaw |

(Continued)

FOREIGN PATENT DOCUMENTS

| | | |
|---|---|---|
| EP | 1214386 B1 | 1/2004 |
| EP | 2327750 B1 † | 3/2013 |

(Continued)

OTHER PUBLICATIONS

Paul, Charles W. "Chapter 15—Hot melt adhesives" Surfaces, Chemistry and Applications: Adhesion Science and Engineering, Chaudhury M and Pocius AV (ed), Elsevier Science B.V., The Netherlands, pp. 711-757.

(Continued)

*Primary Examiner* — Jeremy R Pierce
*Assistant Examiner* — Christine X Nisula
(74) *Attorney, Agent, or Firm* — Sun Hee Lehmann

(57) ABSTRACT

The disclosure relates to adhesive compositions comprising a semi-crystalline olefin polymer or copolymer and a functionalized wax, functionalized olefin polymer, or mixture thereof. These compositions are useful as, for example, adhesives in disposable articles such as diapers, adult incontinence articles, underpads, personal care garments, and the like.

7 Claims, No Drawings

(56) References Cited

U.S. PATENT DOCUMENTS

| | | | |
|---|---|---|---|
| 8,853,329 | B2 | 10/2014 | Kasper et al. |
| 2004/0127614 | A1 † | 7/2004 | Jiang |
| 2009/0203847 | A1 | 8/2009 | Ellis et al. |
| 2010/0179268 | A9 * | 7/2010 | Jiang ................ C08L 91/06 525/70 |
| 2011/0021103 | A1 | 1/2011 | Alper et al. |
| 2012/0016086 | A1 | 1/2012 | Kasper et al. |
| 2012/0329353 | A1 | 12/2012 | Davis et al. |
| 2013/0060215 | A1 * | 3/2013 | Knutson ............ C09J 123/142 524/323 |
| 2013/0203900 | A1 | 8/2013 | Ellis et al. |
| 2014/0147669 | A1 | 5/2014 | Thatcher et al. |
| 2014/0199545 | A1 | 7/2014 | Moriguchi et al. |
| 2014/0199907 | A1 | 7/2014 | Moriguchi et al. |
| 2014/0199908 | A1 | 7/2014 | Inoue |
| 2014/0235127 | A1 | 8/2014 | DeJesus et al. |
| 2014/0324006 | A1 † | 10/2014 | Zhong |
| 2014/0350155 | A1 | 11/2014 | Hamann et al. |
| 2014/0358100 | A1 | 12/2014 | Remmers et al. |
| 2015/0166849 | A1 | 6/2015 | Inoue |
| 2015/0259578 | A1 | 9/2015 | Jones et al. |
| 2015/0368522 | A1 * | 12/2015 | Fujinami ............... C08L 23/06 525/240 |
| 2016/0121014 | A1 | 5/2016 | Remmers et al. |
| 2016/0230055 | A1 | 8/2016 | Hamann et al. |
| 2017/0198176 | A1 | 7/2017 | Kamochi et al. |
| 2018/0191042 | A1 | 7/2018 | Chu |
| 2018/0312733 | A1 | 11/2018 | Ricci Mingani et al. |
| 2020/0140726 | A1 | 5/2020 | Mosanu et al. |

FOREIGN PATENT DOCUMENTS

| | | |
|---|---|---|
| RU | 2433144 C2 | 11/2011 |
| WO | 9709393 A1 | 3/1997 |
| WO | 2011025587 A1 | 3/2011 |
| WO | 2013019507 A2 | 2/2013 |
| WO | 2013039262 A1 † | 3/2013 |
| WO | 2014034916 A1 | 3/2014 |
| WO | 2014190098 A1 † | 11/2014 |

OTHER PUBLICATIONS

"The Performance of L-MODU(TM) for HMA Base Polymer Use" Idemitsu Kosan Co., Ltd., Nov. 2014, retrieved from http://www.idemitsu.com/content/100165495.pdf.

Eastotac Hydrocarbon Resins Brochure by the Eastman Company (Aug. 1992).

Specialty Polymers for Adhesives and Sealants by the Exxon Chemical Company (Oct. 1990).

Litz, R.J., Developments in Ethylene-Based Hot Melt Adhesives, Adhesives Age 17(8):35-38 (1974).

Clark, T., Bookbinding with Adhesives (3rd ed. McGraw-Hill, UK 1994), p. 1.

Alger, Mark S.M., Polymer Science Dictionary (Elsevier Applied Science, New York 1989), p. 115.

Lee, S.M., Dictionary of Composite Materials Technology (Technomic Publishing Company, Inc., 1989) p. 43.

Young, R.J. & Lovell, P.A., Introduction to Polymers (2nd ed., Chapman & Hall, New York 1991), pp. 10-11, 292.

Handbook of Adhesives (ed. Irving Skeist, Van Nostrand Reinhold Co. 1977), pp. 495-498.

Kraus et al., Tack and Viscoelasticity of Block Copolymer Based Adhesives, J. Adhesion 10:221-36 (1979).

Eastman Chemical Brochure titled "World of Eastman Chemicals" dated Jan. 1989, Publication No. P-160F.

Eastman AQ Branched Polyesters Brochure dated Sep. 1997, Publication No. WA-62B.

Eastman Chemical Sales Brochure dated Feb. 1993, Publication No. WA-21.

Exxon Chemical Sales Brochure dated Mar. 1994.

Eastman Chemical Eastotac Hydrocarbon Resins dated Nov. 1994, Publication WA-3C.

Exxon Chemical Escorez Tackifiers Brochure dated Apr. 1992.

\* cited by examiner
† cited by third party

HOT MELT ADHESIVES AND USES THEREOF

BACKGROUND OF THE INVENTION

Many conventional hot melt adhesives for elastic applications are based on styrene block copolymers. These block copolymers provide elasticity and strength through incorporation of an elastomeric mid-block (e.g., isoprene) and a hard domain end block (e.g., styrene). But in order to apply these adhesives at an appropriate temperature and viscosity, the polymer content is minimized in favor of higher levels of tackifiers and plasticizers.

Olefin-based chemistry has been explored for use in elastic applications but its use has been limited in view of the lack of balance in cohesive/adhesive strength. For example, while an initial creep resistance can sometimes be achieved, that creep resistance is dramatically reduced after thermal aging, resulting in an adhesive that can no longer hold strands in place.

There is a need for olefin-based adhesive compositions that possess and maintain the elastic performance characteristics of a conventional styrene block copolymer, even after thermal aging.

SUMMARY OF THE INVENTION

The present disclosure is directed to stretch adhesive compositions comprising about 25 wt. % to about 75 wt. %, by weight of the stretch adhesive composition, of a semi-crystalline propylene polymer that is a homo-polymer or co-polymer characterized by a heat of fusion ($\Delta$Hm) of between about 4 J/g and about 30 J/g; a storage modulus (E') at 40° C. and 1 Hz of between about $3.0 \times 10^8$ dyn/cm$^2$ and about $1.7 \times 10^9$ dyn/cm$^2$; and a viscosity ($\eta$) at 200° C. of between about 2 Pa·s and about 100 Pa·s. The stretch adhesive compositions also comprise between about 1 wt. % and about 10 wt. %, by weight of the stretch adhesive composition, of an adhesion promoter that is a functional wax, functionalized polyolefin, functionalized tackifier, functionalized plasticizer, or a mixture thereof; and between about 10 wt. % and about 55 wt. %, by weight of the stretch adhesive composition, of a tackifier. Methods of making and using these stretch adhesive compositions is also described.

DETAILED DESCRIPTION OF THE INVENTION

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present disclosure. All publications, patent applications, patents and other references mentioned herein are incorporated by reference in their entirety. The materials, methods, and examples disclosed herein are illustrative only and not intended to be limiting.

As used in the specification and in the claims, the term "comprising" may include the embodiments "consisting of" and "consisting essentially of." The terms "comprise(s)," "include(s)," "having," "has," "can," "contain(s)," and variants thereof, as used herein, are intended to be open-ended transitional phrases, terms, or words that require the presence of the named ingredients/steps and permit the presence of other ingredients/steps. However, such description should be construed as also describing compositions or processes as "consisting of" and "consisting essentially of" the enumerated ingredients/steps, which allows the presence of only the named ingredients/steps, along with any impurities that might result therefrom, and excludes other ingredients/steps.

Numerical values in the specification and claims of this application, particularly as they relate to polymers or polymer compositions, reflect average values for a composition that may contain individual polymers of different characteristics. Furthermore, unless indicated to the contrary, the numerical values should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 to 10" is inclusive of the endpoints, 2 and 10, and all the intermediate values). The endpoints of the ranges and any values disclosed herein are not limited to the precise range or value; they are sufficiently imprecise to include values approximating these ranges and/or values.

As used herein, approximating language may be applied to modify any quantitative representation that may vary without resulting in a change in the basic function to which it is related. Accordingly, a value modified by a term or terms, such as "about," may not be limited to the precise value specified, in some cases. In at least some instances, the approximating language may correspond to the precision of an instrument for measuring the value. The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

The present disclosure is directed to stretch adhesive compositions. These adhesive compositions comprise about 25 wt. % to about 75 wt. %, by weight of the adhesive composition, of a semi-crystalline propylene polymer, which can be a homo-polymer or a co-polymer; between about 1 wt. % and about 10 wt. %, by weight of the adhesive composition, of an adhesion promoter that is a functionalized wax, a functionalized polyolefin, functionalized tackifier, functionalized plasticizer, or a mixture thereof; and between about 10 wt. % and about 55 wt. %, by weight of the adhesive composition, of a tackifier. These adhesive compositions exhibit, for example, desirable creep performance, even after exposure to long-term aging conditions.

The term "semi-crystalline" used for the propylene polymers refers to those polymeric materials that contain both crystalline and amorphous regions in the solid state. In the crystalline region, the molecular chains of the polymers are all arranged in ordered three-dimensional arrays whose structure can be fully characterized by their unit cells, the smallest structural unit used to describe a crystal. The amorphous polymers, in contrast, do not have ordered three-dimensional structures in the solid state. Their molecular chains are arranged in a completely random fashion in space. Semi-crystalline polymers can be easily distinguished from completely amorphous polymers by observing the presence or absence of a melting point (Tm) and the associated enthalpy or heat of melting (ΔHm) derived from the transformation of the crystalline state to liquid state upon heating. All semi-crystalline polymers exhibit a melting point, whereas the melting point is absent for amorphous polymers. Amorphous polymers undergo a transition from a glassy solid to a rubbery elastic state in a narrow temperature range around a glass transition temperature Tg. One should not confuse the glass transition temperature Tg with the melting point Tm. Unlike the melting transition of the crystalline materials, the glass transition of amorphous polymers do not have an enthalpy change (ΔH) associated with it.

It should be noted that semi-crystalline polymers defined above are often referred to as crystalline polymers in the trade. Except for the single crystals prepared in the laboratories on a small scale, perfect crystalline polymers are not encountered in the commercial world and all so-called crystalline polymers, strictly speaking, are semi-crystalline. The definition of semi-crystalline polymers set forth herein, therefore, embraces the term "crystalline polymers".

Since semi-crystalline polymers contain both crystalline and amorphous regions, in addition to melting transition of crystals, they can exhibit a glass transition associated with the amorphous region of the material. The glass transition takes place at a temperature below the melting point.

The enthalpy or heat of fusion (ΔHm) can be determined by Differential Scanning calorimetry (DSC). The technique is well known to those skilled in the art and is well described in the scientific literature.

The semi-crystalline propylene polymers of the disclosure are homo-polymers or co-polymers. These semi-crystalline propylene polymers are characterized by particular heats of fusion (ΔHm), storage modulus (E'), and viscosity (η), as described herein.

The semi-crystalline propylene polymers are characterized, in part, by a heat of fusion, measured according to ASTM D3418-12, of between about 4 J/g and about 30 J/g. For example, the semi-crystalline propylene polymers of the disclosure are characterized by a heat of fusion of about 4, 5, 6, 7, 8, 9, 10, 11, 12, 13, 14, 15, 16, 17, 18, 19, 20, 21, 22, 23, 24, 25, 26, 27, 28, 29, or 30 J/g, or any range thereof. In some embodiments of the disclosure, the semi-crystalline propylene polymers are characterized by a heat of fusion of between about 4 J/g and about 6 J/g. In other embodiments, the semi-crystalline propylene polymers are characterized by a heat of fusion of between about 20 J/g and about 24 J/g.

The semi-crystalline propylene polymers are also characterized, in part, by a storage modulus (E'), measured at 40° C. and 1 Hz, of between about $3.0 \times 10^8$ dyn/cm$^2$ and about $1.7 \times 10^9$ dyn/cm$^2$. Methods of measuring storage modulus are known in the art and are described herein. For example, the semi-crystalline propylene polymers of the disclosure are characterized by a storage modulus of about $3.0 \times 10^8$, $3.5 \times 10^8$, $4.0 \times 10^8$, $4.5 \times 10^8$, $5.0 \times 10^8$, $5.5 \times 10^8$, $6.0 \times 10^8$, $6.5 \times 10^8$, $7.0 \times 10^8$, $7.5 \times 10^8$, $8.0 \times 10^8$, $8.5 \times 10^8$, $9.0 \times 10^8$, $9.5 \times 10^8$, $1.0 \times 10^9$, $1.1 \times 10^9$, $1.2 \times 10^9$, $1.3 \times 10^9$, $1.4 \times 10^9$, $1.5 \times 10^9$, $1.6 \times 10^9$, or $1.7 \times 10^9$ dyn/cm$^2$, or any range thereof. In some preferred embodiments, the semi-crystalline propylene polymers are characterized by a storage modulus of between about $5.0 \times 10^8$ dyn/cm$^2$ to about $1.1 \times 10^9$ dyn/cm$^2$.

The semi-crystalline propylene polymers are also characterized, in part, by a viscosity, as measured at 200° C., using ASTM D3236, of between about 2 Pa·s and about 100 Pa·s. For example, the semi-crystalline propylene polymers of the disclosure are characterized by a viscosity of about 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, or 100 Pa·s, or any range thereof. In preferred embodiments, the semi-crystalline propylene polymers are characterized by a viscosity of between about 2 Pa·s and about 25 Pa·s or about 5 Pa·s and about 25 Pa·s. In preferred embodiments, the semi-crystalline propylene polymers are characterized by a viscosity of between about 2 Pa·s and about 8 Pa·s or about 5 Pa·s and about 8 Pa·s. In other embodiments, the semi-crystalline propylene polymers are characterized by a viscosity of between about 20 Pa·s and about 24 Pa·s.

In some embodiments of the disclosure, the semi-crystalline propylene polymer is a homo-polymer. Preferred semi-crystalline propylene homo-polymers have medium range tacticity (stereo-regularity) with narrow and homogenous molecular weight distribution. Such polymers allow for adequate processability and rigidity, and are useful as components in adhesive applications. Polymers having medium range tacticity can be differentiated from isotactic and atactic polymers, as described in a presentation titled "The Performance of L-MODU™ for HMA Base Polymer Use" by Idemitsu Kosan Co., Ltd dated November 2014, retrieved from http://www.idemitsu.com/content/100165495.pdf. Isotactic semi-crystalline propylene homo-polymer have high tacticity and are usually very rigid due to the high levels of crystallinity in the polymer structure, which make them undesirable for use in adhesives applications. Polymers with medium range tacticity are available; however, they typically have broad molecular weight distributions that compromise processability when used as a component in adhesives. One non-limiting method to control and prepare medium tacticity stereo-regularity and narrow and homogeneous molecular weight polymers is with a metallocene catalyst. Such semi-crystalline propylene homo-polymers having the characteristics described herein can be purchased from commercial sources or can be prepared according to methods described in the art. One preferred semi-crystalline propylene homo-polymer is L-MODU S-400, available from Idemitsu Kosan Co., Ltd. Other semi-crystalline propylene polymers of interest are S-600 and S-901, also available from Idemitsu. Other semi-crystalline homopolymers with storage modulus and viscosity within the ranges described herein can also be used in this invention.

In some embodiments of the disclosure, the semi-crystalline propylene polymer is a co-polymer. Semi-crystalline propylene co-polymers having the required characteristics can be prepared according to methods described in the art, for example, in U.S. Pat. No. 8,853,329 and U.S. Publication No. 2014/0235127, the entireties of which are incorporated by reference herein.

The adhesive compositions of the disclosure comprise about 25 wt. % to about 75 wt. %, by weight of the adhesive composition, of the semi-crystalline propylene polymer. For example, the adhesive compositions of the disclosure comprise about 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, or 75 wt. %, or any range thereof, by weight of the adhesive composition, of the semi-crystalline propylene polymer. Preferred embodiments include about 30 wt. % to about 60 wt. %, by weight of the adhesive composition, of the semi-crystalline propylene polymer.

The adhesive compositions of the disclosure include between about 1 wt. % and about 10 wt. %, by weight of the adhesive composition, of an adhesion promoter. These adhesion promoters can be, for example, a functional wax, a functional polyolefin, or a mixture thereof. These adhesion promoters can alternatively be a functionalized wax, a functionalized polyolefin, a functionalized tackifier, a functionalized plasticizer, a functional rubber or a mixture thereof. The adhesion promoter may be present in amounts from about 1 to about 10 wt. %, preferably from 1 wt. % to 5 wt. % or from 1 wt. % to 3 wt. %, based on the total weight of the adhesive composition. For example, the adhesive compositions of the invention can include 1, 1.5, 2, 2.5, 3, 3.5, 4, 4.5, 5, 5.5, 6, 6.5, 7, 7.5, 8, 8.5, 9, 9.5, or 10 wt. %, or any range thereof, of the adhesion promoter, based on the total weight of the adhesive composition.

The functional groups are present on the backbones of polyolefin polymers, rubbers, waxes, tackifiers, plasticizers or mixtures thereof. The functional groups may be incorporated by, for example but not limited to, grafting, copolymerizing or endcapping the functional group onto the backbone. Suitable functional groups include, for example, carboxylic acid, carboxylic acid esters, anhydride, hydroxyl, thiol, epoxy, amine, urethane, urea, ureido, silane and sulfonate groups. Specific functional groups include silanes, acrylic acid or methacrylic acid, tert-butyl(meth)acrylate, crotonic acid, acrylic acid, acetate, sulfonate, citraconic anhydride, fumaric acid, maleic acid, and itaconic acid, mono- or di-tert-butyl crotonate, mono- or di-tert-butyl fumarate and mono- or di-tert-butyl maleate, maleic anhydride, p-styrenesulfonic acid, 2-(meth)acrylamide-2-methylpropenesulfonic acid, 2-sulfonyl(meth)acrylate, vinyloxazolines, glycidyl(meth)acrylate, allyl glycidyl ether, and the like. The functional group may be present in amounts from about 0.1 to about 10 wt. %, preferably up to 8 wt. % or up to 5 wt. %, based on the total weight of the functionalized polyolefin polymers, rubbers, waxes, tackifiers or plasticizers. For example, the functional group can include, 0.1, 0.2, 0.3, 0.4, 0.5, 0.6, 0.7, 0.8, 0.9, 1, 2, 3, 4, 5, 6, 7, 8, 9 or 10 wt. %, or any range thereof, of the functional group, based on the total weight of the functionalized polyolefin polymers, rubbers, waxes, tackifiers or plasticizers.

Representative examples of polyolefins include homopolymers and copolymers of various olefins such as ethylene, propylene, butylene, pentene, hexylene, heptene and octene. Suitable functional groups onto these polyolefins to form the functional polyolefins of the disclosure include, for example, include, for example, carboxylic acid, carboxylic acid esters, anhydride, hydroxyl, thiol, epoxy, amine, urethane, urea, ureido, silane and sulfonate groups. Specific functional groups include silanes, acrylic acid or methacrylic acid, tert-butyl(meth)acrylate, crotonic acid, acrylic acid, acetate, sulfonate, citraconic anhydride, fumaric acid, maleic acid, and itaconic acid, mono- or di-tert-butyl crotonate, mono- or di-tert-butyl fumarate and mono- or di-tert-butyl maleate, maleic anhydride, p-styrenesulfonic acid, 2-(meth)acrylamide-2-methylpropenesulfonic acid, 2-sulfonyl(meth)acrylate, vinyloxazolines, glycidyl(meth)acrylate, allyl glycidyl ether, and the like.

Representative examples of waxes include homopolymers and copolymers of various olefins such as ethylene, propylene, butylene, pentene, hexylene, heptene and octene. The wax can be of natural or synthetic origin. Naturally occurring waxes include vegetable waxes, animal waxes, mineral waxes, and petrochemical waxes. Suitable functional groups onto these waxes to form the functionalized waxes of the disclosure include, for example, carboxylic acid, carboxylic acid esters, anhydride, hydroxyl, thiol, epoxy, amine, urethane, urea, ureido, silane, and sulfonate groups. Specific functional groups include silanes, acrylic acid or methacrylic acid, tert-butyl(meth)acrylate, crotonic acid, acrylic acid, acetate, sulfonate, citraconic anhydride, fumaric acid, maleic acid, and itaconic acid, mono- or di-tert-butyl crotonate, mono- or di-tert-butyl fumarate and mono- or di-tert-butyl maleate, maleic anhydride, p-styrenesulfonic acid, 2-(meth)acrylamide-2-methylpropenesulfonic acid, 2-sulfonyl(meth)acrylate, vinyloxazolines, glycidyl(meth)acrylate, allyl glycidyl ether, and the like.

Fundamentally, the functionalized polyolefin and functionalized wax can both be homopolymers and copolymers of various olefins such as, but not limited to, ethylene, propylene, butylene, pentene, hexylene, heptene and octene containing functional groups described herein. One way to differentiate a polymer from a wax is by the molecular weight. Polymers typically have a number average molecular weight of about 5000 g/mol or greater while waxes have a molecular weight of about 5000 g/mol or less.

Alternatively, functional groups used to prepare the functionalized waxes of the disclosure exclude carboxylic acid and/or anhydride. These alternative functionalized waxes are also known herein as non-carboxylic acid and/or anhydride functionalized waxes.

In one embodiment, the functionalized wax used in the practice of the invention is a maleic anhydride grafted on a polypropylene wax. A variety of maleic anhydride grafted wax suitable for use herein is available commercially and/or are obtainable using known procedures. For example, maleated polyethylenes are available from Honeywell under the trade names A-C 575 and A-C 573, and from DuPont as products listed as part of their Fusabond E series. Maleated polypropylenes are available from Honeywell under the trade names A-C 597A, A-C 597P, A-C 907P, A-C 596A, A-C 596P, A-C 950P and A-C 1325P, from DuPont as products listed under the Fusabond P trade named series, from Eastman under the trade names G-3015, G-3003, and from Westlake under the trade name EPOLENE E-43. Any known procedures for producing maleated polyolefins from precursor compounds can be adapted for use to make starting materials suitable for use herein. For example, U.S. Pat. No. 7,256,236, incorporated herein by reference, discloses certain preferred methods for producing maleated polypropylenes suitable for use herein.

In another embodiment, the functionalized wax is a wax that has been copolymerized with a functional group. Representative examples of suitable copolymerized waxes include terpolymer of ethylene-acrylic ester-maleic anhydride and ethylene-acrylic ester-glycidyl methacrylate, available as LOTADER® MAH and LOTADER® GMA, respectively.

In another embodiment, the functionalized wax is a copolymer of Ethylene-Acrylic acid such as the ones available from Honeywell under the trade names A-0540, A-0580, A-05120, and A-C 5180.

In a further embodiment, the functionalized wax is an oxidized polyethylene homopolymers, including high density oxidized polyethylene homopolymers. Exemplary oxidized polyethylenes are available from Honeywell under the trade names A-C 673P, A-C 680, A-C 655, A-C 629, A-C 629A, A-C 656, A-C 6702, A-C 307, A-C 307A, A-C 316, A-C316A, A-C 325, A-C 392, A-C 330, A-C 395 and A-C 395A.

In addition to functionalized polymers or waxes, other common raw materials used in the making of an adhesive that contain functional groups could be used in this invention. Polar tackifiers that contain functional groups such as rosin ester for example the partially hydrogenated rosin produced by Eastman as Staybelite Resin-E and completely hydrogenated rosin as Foral AX-E. Maleic anhydride modified rosin ester known as Lewisol from Eastman is also of interest in this invention. Other polar tackifiers such as polyterpene phenolics produced by Arizona as Sylvarez TP or AMS phenolic resin produced by Arizona as Sylvarez can also be used as adhesion promoters in the described compositions. Polar liquid plasticizers can also be used as adhesion promoters in the described compositions, for example plasticizers derived from rosin ester acid such as Abitol E from Eastman or citrate based such as Citroflex 4 from Vertellus Performance Materials.

The adhesive compositions of the disclosure also include between about 10 wt. % and about 55 wt. %, by weight of the adhesive composition, of a tackifier, i.e., a "tackifiying resin" or "non-functionalized tackifier." "Tackifying resins" are understood to mean in particular polymeric additives that increase their autoadhesion (tack, inherent tack, self-adhesion). For example, the adhesive compositions of the disclosure include about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55 wt. %, or any range thereof, by weight of the adhesive composition, of a tackifier. In preferred embodiments, the adhesive compositions of the disclosure include between about 20 wt. % and about 55 wt. %, by weight of the adhesive composition, of a tackifier.

Typical tackifiers have Ring and Ball softening points, as determined by ASTM method E28, of about 70° C. to about 180° C., more preferably about 95° C. to about 150° C. Useful tackifying resins may include any compatible resin or mixtures thereof, such as natural and modified rosins including, for example, as gum rosin, wood rosin, tall oil rosin, distilled rosin, hydrogenated rosin, dimerized rosin, resinates, and polymerized rosin; glycerol and pentaerythritol esters of natural and modified rosins, including, for example, the glycerol ester of pale, wood rosin, the glycerol ester of hydrogenated rosin, the glycerol ester of polymerized rosin, the pentaerythritol ester of hydrogenated rosin, and the phenolic-modified pentaerythritol ester of rosin; copolymers and terpolymers of natured terpenes, including, for example, styrene/terpene and alpha methyl styrene/terpene; polyterpene resins having a softening point, as determined by ASTM method E28, from about 70° C. to about 150° C.; phenolic modified terpene resins and hydrogenated derivatives thereof including, for example, the resin product resulting from the condensation, in an acidic medium, of a bicyclic terpene and a phenol; aliphatic petroleum hydrocarbon resins having a Ball and Ring softening point from about 70° C. to about 135° C.; aromatic petroleum hydrocarbon resins and the hydrogenated derivatives thereof; and alicyclic petroleum hydrocarbon resins and the hydrogenated derivatives thereof. Examples of hydrogenated tackifiers particularly suitable include Escorez 5400 from Exxon Mobil Chemicals, Arkon PI 00 from Arakawa and Regalite SI 100 from Eastman Chemical, and the like. Also included are the cyclic or acyclic C5 resins and aromatic modified acyclic or cyclic resins. Examples of commercially available rosins and rosin derivatives that could be used to practice the invention include SYLVALITE RE 1 10 L, SYLVARES RE 115, and SYLVARES RE 104 available from Arizona Chemical; Dertocal 140 from DRT; Limed Rosin No. I, GB-120, and Pencel C from Arakawa Chemical. Examples of commercially available phenolic modified terpene resins are Sylvares TP 2040 HM and Sylvares TP 300, both available from Arizona Chemical.

Preferred tackifiers are synthetic hydrocarbon resins. Included are aliphatic or cycloaliphatic hydrocarbons, aromatic hydrocarbons, aromatically modified aliphatic or cycloaliphatic hydrocarbons and mixtures thereof.

Non-limiting examples include aliphatic olefin derived resins such as those available from Goodyear under the Wingtack Extra trade name and the Escorez 1300 series from Exxon. A common C5 tackifying resin in this class is a diene-olefin copolymer of piperylene and 2-methyl-2-butene having a softening point of about 95° C. This resin is available commercially under the trade name Wingtack 95. Eastotac series from Eastman are also useful in the invention.

Also useful are aromatic hydrocarbon resins that are C9 aromatic/aliphatic olefin-derived and available from Sartomer and Cray Valley under the trade name Norsolene and from Rutgers series of TK aromatic hydrocarbon resins. Norsolene MI 090 is a low molecular weight thermoplastic hydrocarbon polymer having a Ring and Ball softening point of 95-105° C. and is commercially available from Cray Valley.

Alpha methyl styrene such as Kristalex 3085 and 3100 from Eastman Chemicals, Sylvares S A 100 from Arizona chemicals are also useful as tackifiers in the invention. Mixtures of two or more described tackifying resins may be required for some formulations.

Small quantities of alkyl phenolic tackifiers can be blended with additional tackifier agents detailed above to improve the high temperature performance of these adhesives. Alkyl phenolics added in less than 20 wt. % of the total weight of the adhesive are compatible and in the proper combination increase high temperature adhesive performance. Alkyl phenolics are commercially available from Arakawa Chemical under the Tamanol trade name and in several product lines from Schenectady International.

The adhesive compositions of the disclosure may optionally further comprise up to 10 wt. %, by weight of the adhesive composition, of a solid plasticizer or a liquid plasticizer. For example, the adhesive compositions of the disclosure may comprise 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, or 10 wt. % of a solid plasticizer or a liquid plasticizer. Suitable plasticizers include paraffinic oil, naphthenic oil, aromatic oil, long chain partial ether ester, alkyl monoesters, epoxidized oils, dialkyl diesters, aromatic diesters, alkyl ether monoester, polybutenes, phthalates, benzoates, adipic esters and the like. Solid plasticizers, for example those derived from 1,4-cyclohexane dimethanol dibenzoate, available from Eastman Chemical under the name of BENZOFLEX can also be used in the described compositions. Particularly preferred plasticizers include mineral oil, aliphatic oils, polybutene, polyisobutylene, olefin oligomers and low molecular weight polymers, vegetable oil, animal oils and derivatives.

The adhesive compositions of the disclosure may optionally further include up to 10 wt. %, for example, 0.1 wt. % to about 10 wt. %, preferably about 2 wt. % to about 8 wt. %, by weight of the adhesive composition, of a non-functionalized wax. For example, the adhesive compositions of the disclosure can comprise 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, or 10 wt. %, or any range thereof, by weight of the adhesive composition, of a non-functionalized wax. Representative examples of suitable waxes include homopolymers and copolymers of various olefins such as ethylene, propylene, butylene, pentene, hexylene, heptene and octene. The wax can be of natural or synthetic origin. Naturally occurring waxes that can be added are vegetable waxes, animal waxes, mineral waxes or petrochemical waxes.

Paraffin waxes that can be used in the practice of the invention include PACEMAKER® 30, 32, 35, 37, 40, 42, 45

& 53 available from Citgo Petroleum, Co.; ASTOR OKERIN® 236 available from Honeywell; R-7152 Paraffin Wax available from Moore & Munger; R-2540 available from Moore and Munger; and other paraffinic waxes such as those available from Sasol Wax under the product designations Sasolwax 5603, 6203 and 6805.

The microcrystalline waxes useful here are those having 50 percent by weight or more cyclo or branched alkanes with a length of between 30 and 100 carbons. They are generally less crystalline than paraffin and polyethylene waxes, and have melting points of greater than about 70° C. Examples include VICTORY® Amber Wax, a 70° C. melting point wax available from Baker Petrolite Corp.; BARECO® ES-796 Amber Wax, a 70° C. melt point wax available from Bareco; BESQUARE® 175 and 195 Amber Waxes and 80° C. and 90° C. melt point microcrystalline waxes both available from Baker Petrolite Corp.; Indramic® 91, a 90° C. melt point wax available from Industrial Raw Materials; and PETROWAX® 9508 Light, a 90° C. melt point wax available from Petrowax. Other examples of microcrystalline waxes are Sasolwax 3971 available from Sasol Wax and Microwax K4001 available from Alfred Kochem GmBH.

Exemplary high density low molecular weight polyethylene waxes falling within this category include ethylene homopolymers available from Backer Petrolite Corp. as POLYWAX™ 500, POLYWAX™ 1500 and POLYWAX™ 2000. POLYWAX™ 2000 has a molecular weight of approximately 2000, an Mw/Mn of approximately 1.0, a density at 16° C. of about 0.97 g/cm$^3$, and a melting point of approximately 126° C. Other examples of polyethylene homopolymer waxes are AC 9, 9A, 9F, 8, 8A, AC 7, 7A, etc., available from Honeywell.

The adhesive compositions of the disclosure may optionally further comprise up to 2.5 wt. %, for example, 0.1 wt. % to 2.5 wt. %, preferably about 0.2 wt. % to about 2.0 wt. %, by weight of the adhesive composition, of one or more of an antioxidant, stabilizer, crosslinking agent, filler, nucleating agent, adhesion promoter, elastomer, colorant, rheology modifier, or a mixture thereof. For example, the adhesive compositions of the disclosure may include 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2.0, 2.1, 2.2, 2.3, 2.4, 2.5 wt. %, or any range thereof, by weight of the adhesive composition, of one or more of an antioxidant, stabilizer, crosslinking agent, filler, nucleating agent, elastomer, colorant, rheology modifier, or a mixture thereof.

Applicable stabilizers or antioxidants included herein are high molecular weight hindered phenols and multifunctional phenols such as sulfur and phosphorus-containing phenol. Hindered phenols are well known to those skilled in the art and may be characterized as phenolic compounds which also contain sterically bulky radicals in close proximity to the phenolic hydroxyl group thereof. In particular, tertiary butyl groups generally are substituted onto the benzene ring in at least one of the ortho positions relative to the phenolic hydroxyl group. The presence of these sterically bulky substituted radicals in the vicinity of the hydroxyl group serves to retard its stretching frequency, and correspondingly, its reactivity; this hindrance thus provides the phenolic compound with its stabilizing properties. Representative hindered phenols include; 1,3,5-trimethyl-2,4,6-tris-(3,5-di-tert-butyl-4-hydroxybenzyl)-benzene; pentaerythrityl tetrakis-3(3,5-di-tert-butyl-4-hydroxyphenyl)-propionate; n-octadecyl-3(3,5-ditert-butyl hydroxyphenyl)-propionate; 4,4'-methylenebis(2,6-tert-butyl-phenol); 4,4'-thiobis(6-tert-butyl-o-cresol); 2,6-di-tertbutylphenol; 6-(4-hydroxyphenoxy)-2,4-bis(n-octyl-thio)-1,3,5 triazine; di-n-octylthio)ethyl 3,5-di-tert-butyl-4-hydroxy-benzoate; and sorbitol hexa[3-(3,5-ditert-butyl-4-hydroxy-phenyl)-propionate].

Such antioxidants are commercially available from BASF and include Irganox® 565, 1010, 1076 and 1726 which are hindered phenols. These are primary antioxidants that act as radical scavengers and may be used alone or in combination with other antioxidants, such as, phosphite antioxidants like IRGAFOS® 168 available from BASF. Phosphite antioxidants are considered secondary antioxidants and are not generally used alone. These are primarily used as peroxide decomposers. Other available catalysts are CYANOX® LTDP available from Cytec Industries and ETHANOX® 330 available from Albemarle Corp. Many such antioxidants are available either to be used alone or in combination with other such antioxidants. These compounds are added to the hot melts in small amounts, typically less than about 10 wt. %, and have no effect on other physical properties. Other compounds that could be added that also do not affect physical properties are pigments, which add color, or fluorescing agents. Additives like these are known to those skilled in the art.

In general, stabilizers are incorporated in order to protect the adhesive as the end product of the process according to the invention against oxidative or thermal degradation reactions that can occur in storage and/or application. The usable stabilizers preferably include hindered phenols and/or multifunctional phenols, such as for example sulfur-containing and/or phosphorus-containing phenols. Hindered phenols are understood to mean compounds, in which at least one sterically hindered group, such as for example a tert-butyl group, is bonded to the phenol, wherein the sterically hindered groups are located especially in the ortho and/or para position to the phenolic OH group. Exemplary hindered phenols that are suitable stabilizers can be selected from the following compounds or from any of their mixtures: 1,3,5-trimethyl-2,4,6-tris(3,5-di-tert.-butyl-4-hydroxybenzyl)benzene, pentaerythritol tetrakis-(3,5-di-tert.-butyl hydroxyphenyl)propionate, n-octadecyl-(3,5-di-tert.-butyl-4-hydroxyphenyl)propionate, 4,4'-methylene bis(4-methyl-6-tert.-butylphenol), 4,4'-thiobis(6-tert.-butyl-o-resol), 2,6-di-tert.-butylphenol, 6-(4-hydroxyphenoxy)-2,4-bis(n-octylthio)-1,3,5-triazine, 2,4,6-tris(4-hydroxy-3,5-di-tert.-butylphenoxy)-1,3,5-triazine, di-n-octadecyl-3,5-di-tert.-butylbenzyl phosphonate, 2-(n-octylthio)ethyl-3,5-di-tert.-butyl-4-hydroxybenzoate and sorbitol hexa-(3,3,5-di-tert.-butyl hydroxyphenyl)propionate.

Further additives can be added, such as for example crosslinking agents, fillers, nucleating agents, elastomers, colorant, rheology modifiers which are known to the person skilled in the art and can be selected from a great number of commercially available products as a function of the desired properties. Additional polymers can be added to modify the adhesive properties. These polymers can be any of the conventional hot melt polymers as described in: Paul C W (2002) Hot Melt Adhesives in: Chaudhury M and Pocius A V (ed) Surfaces, Chemistry and Applications: Adhesion Science and Engineering, Elsevier Science B. V., The Netherlands pp 711-757.

The adhesive compositions of the disclosure exhibit a viscosity at 150° C., as measured according to ASTM D3236 of between about 7500 cPs and about 15,000 cPS. For example, adhesive compositions of the disclosure exhibit a viscosity at 150° C. of about 7500; 8000; 8500; 9000; 9500; 10,000; 10,500; 11,000; 11,500; 12,000; 12,500; 13,000; 13,500; 14,000; 14,500; or 15,000 cPs, or any range thereof.

The adhesive compositions of the disclosure exhibit a shear modulus (G'), also known as shear storage modulus, at 40° C. and 10 rad/s, as measured according to the methods described herein, of between about $1.5 \times 10^6$ dyn/cm$^2$ to about $2.5 \times 10^7$ dyn/cm$^2$. For example, the adhesive compositions of the disclosure exhibit a sheer modulus at 40° C. of about $1.5 \times 10^6$, $2 \times 10^6$, $2.5 \times 10^6$, $3 \times 10^6$, $3.5 \times 10^6$, $4 \times 10^6$, $4.5 \times 10^6$, $5 \times 10^6$, $5.5 \times 10^6$, $6 \times 10^6$, $6.5 \times 10^6$, $7 \times 10^6$, $7.5 \times 10^6$, $8 \times 10^6$, $8.5 \times 10^6$, $9 \times 10^6$, $9.5 \times 10^6$, $1 \times 10^7$, $1.5 \times 10^7$, $2 \times 10^7$, or $2.5 \times 10^7$ Pa, or any range thereof.

The adhesive compositions of the disclosure exhibit an initial creep resistance that is suitable for use in the described applications. Creep resistance can be measured using the methods described herein. For example, adhesive compositions of the disclosure exhibit an initial creep %, for 25 mg/m/strand, of less than 20%, preferably less than 10%, and even more preferably, less than 7%. For example, adhesive compositions of the disclosure exhibit an initial creep % of between about 2% and 7%. In certain embodiments, the adhesive compositions of the disclosure will exhibit an initial creep % of less than 20%, less than 10%, less than 9%, less than 8%, less than 7%, less than 6%, less than 5%, less than 4%, less than 3%, or less than 2%.

The adhesive compositions of the disclosure exhibit an aged creep % that is suitable for use in the described applications. For example, the adhesive compositions of the disclosure exhibit a creep, after 2 weeks (14 days) at 40° C., for 25 mg/m/strand, of less than 40%, preferably less than 35%. For example, adhesive compositions of the disclosure exhibit a creep, after 2 weeks (14 days) at 40° C. for 25 mg/m/strand, of less than 40%, less than 39%, less than 38%, less than 37%, less than 36%, less than 35%, less than 34%, less than 33%, less than 32%, less than 31%, less than 30%, less than 29%, less than 28%, less than 27%, less than 26%, less than 25%, less than 24%, less than 23%, less than 22%, less than 21%, less than 20%, less than 19%, less than 18%, less than 17%, less than 16%, less than 15%, less than 14%, less than 13%, less than 12%, less than 11%, less than 10%, less than 9%, less than 8%, less than 7%, less than 6%, or less than 5%.

In other embodiments, the adhesive compositions of the disclosure exhibit a creep, after 4 weeks (28 days) at 40° C., for 25 mg/m/strand, of less than 40%, preferably less than 35%. For example, adhesive compositions of the disclosure exhibit a creep, after 4 weeks (28 days) at 40° C. for 25 mg/m/strand, of less than 40%, less than 39%, less than 38%, less than 37%, less than 36%, less than 35%, less than 34%, less than 33%, less than 32%, less than 31%, less than 30%, less than 29%, less than 28%, less than 27%, less than 26%, less than 25%, less than 24%, less than 23%, less than 22%, less than 21%, less than 20%, less than 19%, less than 18%, less than 17%, less than 16%, less than 15%, less than 14%, less than 13%, less than 12%, less than 11%, less than 10%, less than 9%, less than 8%, less than 7%, less than 6%, or less than 5%.

The adhesive compositions of the disclosure exhibit an initial creep resistance that is suitable for use in the described applications. For example, adhesive compositions of the disclosure exhibit an initial creep %, for 35 mg/m/strand, of less than 10%, preferably less than 8% and even more preferably, less than 7%, and most preferably, less than 5%. For example, adhesive compositions of the disclosure exhibit an initial creep %, for 35 mg/m/strand, of between about 1.5% and 3.5%. In certain embodiments, the adhesive compositions of the disclosure will exhibit an initial creep % of less than 10%, less than 9%, less than 8%, less than 7%, less than 6%, less than 5%, less than 4%, less than 3%, or less than 2%.

The adhesive compositions of the disclosure exhibit an aged creep % that is suitable for use in the described applications. For example, the adhesive compositions of the disclosure exhibit a creep, after 2 weeks (14 days) at 40° C., for 35 mg/m/strand, of less than 40%, preferably less than 35%, and more preferably, less than 30%. For example, adhesive compositions of the disclosure exhibit a creep, after 2 weeks (14 days) at 40° C., for 35 mg/m/strand, of less than 40%, less than 39%, less than 38%, less than 37%, less than 36%, less than 35%, less than 34%, less than 33%, less than 32%, less than 31%, less than 30%, less than 29%, less than 28%, less than 27%, less than 26%, less than 25%, less than 24%, less than 23%, less than 22%, less than 21%, less than 20%, less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, or less than 4%.

In other embodiments, the adhesive compositions of the disclosure exhibit a creep, after 4 weeks (28 days) at 40° C., for 35 mg/m/strand, of less than 40%, preferably less than 35%. For example, adhesive compositions of the disclosure exhibit a creep, after 4 weeks (28 days) at 40° C., for 35 mg/m/strand, of less than 40%, less than 39%, less than 38%, less than 37%, less than 36%, less than 35%, less than 34%, less than 33%, less than 32%, less than 31%, less than 30%, less than 29%, less than 28%, less than 27%, less than 26%, less than 25%, less than 24%, less than 23%, less than 22%, less than 21%, less than 20%, less than 19%, less than 18%, less than 17%, less than 16%, less than 15%, less than 14%, less than 13%, less than 12%, less than 11%, less than 10%, less than 9%, less than 8%, less than 7%, less than 6%, or less than 5%.

The adhesive compositions of the present invention are prepared by blending the components in a melt at a temperature above about 180° C. to form a homogeneous blend. Various methods of blending are known in the art and any method that produces a homogeneous blend. The blend is then cooled and may be formed into pellets or blocks for storage or shipping. These pre-formed adhesives can then be reheated to apply onto substrates.

An elastic attachment article is formed by applying the molten elastic attachment adhesive onto a substrate, at an application temperature of about 340° F. (171° C.) or less, preferably less than about 320° F. (160° C.), more preferably less than about 300° F. (149° C.), and placing another substrate onto the molten adhesive, whereby the adhesive is sandwiched in between the two substrates. In another embodiment, a multilayer elastic attachment laminant is formed by applying the molten elastic attachment adhesive onto both sides of a substrate, at an application temperature of about 340° F. (171° C.) or less, preferably less than about 320° F. (160° C.), more preferably less than about 300° F. (149° C.), and placing the substrate in between two additional substrates, whereby the adhesive adheres three substrates together.

The elastic attachment adhesive is typically applied onto a portion of an elastic strand. Non-limiting examples of elastic strand comprise polyester, polyurethane, polyether, polyamide, polyacrylate, polyester-b-polyurethane block copolymer, polyether-b-polyurethane block copolymer or polyether-b-polyamide block copolymer. Suitable elastic multifilament strands include LYCRA (Invista, Inc.) CONFI-FIT™ (Fulflex).

The adhesive according to the invention may be used to bond or laminate the same or different substrates materials to one another. In one embodiment, the elastic strand is attached onto a nonwoven substrate with a basis weight in the range of about 10 to about 35 gsm (g/m$^2$) based on fibers of polyethylene, polypropylene, polyester or cellulose. In another embodiment, the elastic strand is attached to a flexible, elastomeric, sheet-like film. Suitable flexible, elastomer sheet-like film are formed from polyethylene, polypropylene, polyester, polyurethane, polyamide, or combinations thereof, including random or graft copolymers such as styrene block copolymers, polyether-b-polyurethane block copolymer. In another embodiment, the elastic strand is positioned in between one nonwoven substrate and one elastomeric film with the elastomeric attachment adhesive. Yet in another embodiment, the elastic strand is positioned in between two nonwoven substrates with the elastomeric attachment adhesive bonding the nonwovens and strands in place. The add-on level of the elastic attachment adhesive varies, depending on the type of applicators used, but typically ranges from about 2 to about 50 gsm, preferably from about 5 to about 15 gsm for spiral application. The add-on for strand-specific applications, such as OMEGA™ and SUREWRAP®, varies from 20 to 50 milligrams of adhesive/meter/strand. Non-limiting applications include spiral, OMEGA™ (ITW), SUREWRAP® (Nordson), and such techniques are known to those skilled in the art.

Delivery of consistent and uniform adhesive applied onto the elastic strand is an important factor to ensure acceptable performance of the laminant. Adhesives that spray unevenly and inconsistently, e.g., contain polymers with wide molecular weights or that sprays with angel hair fly-aways, typically have poor creep resistance performance as the laminant is stretched and aged. Another important factor is adhesion: the adhesive should remain adhered onto the substrates without failure under strain of deformation. The elastic attachment adhesive of the instant invention sprays evenly and consistently and remains adhered onto the substrates under strain.

The elastic attachment adhesive is well suited for elastic attachment articles. Such articles require low deformation of the adhesive during exposure to heat and strain over a number of hours. It is preferred that the deformation is as small as possible under the heat and strain. One typical method of quantifying the resistance to deformation is by measuring the creep resistance. Creep resistance is a value calculated by measuring the initial creep resistance of the article, and then applying a strain for a specified temperature and time, and then re-measuring the resistance. The elastic attachment adhesive of the instant invention has an initial creep resistance that is less than about 20% after extending the laminated adhesive to 250%-300% at 38° C. for four hours. Moreover, the elastic attachment adhesive has a creep resistance that is less than about 20% after four weeks storage at 40° C. followed by extending the adhesive to 250%-300% strain at 38° C. for four hours.

In order for the elastic attachment adhesive to have an acceptable creep resistance after being aged at 40° C. for up to 4 weeks, the polymer used in the adhesive has to provide enough cohesive strength to keep the lamination held in place during this time. This cohesive strength can be measured via rheology by applying some type of deformation on the sample and recording its response, which is the storage modulus. If the deformation is applied via shear, the shear storage modulus is measured (G'), while if the deformation is applied via compression or tension, the compression/tension storage modulus is measured (E'). The storage modulus, either in shear or compression/tension (E' or G') is related to the stiffness and cohesive strength of the material. It has been discovered that polymers with storage modulus (E') between $3.0 \times 10^8$ to $1.7 \times 10^9$ dyn/cm$^2$, measured at 40° C. and 1 Hz, provide adhesives with excellent creep after being aged for 2 and 4 weeks at 40° C. The overall cohesive strength of adhesive as measured by the storage modulus on shear mode G' was also found to be an important property affecting the aged creep. Adhesives with G', measured at 40° C. and 10 rad/s, ranging from $1.5 \times 10^6$ and about $2.5 \times 10^7$ dyn/cm$^2$ are useful in the described adhesives.

The elastic attachment articles are suitable as absorbent articles such as diapers, diaper pants, baby wipes, training pants, absorbent underpants, child care pants, swimwear, and other disposable garments; feminine care products including sanitary napkins, wipes, menstrual pads, panty liners, panty shields, tampons, and tampon applicators; adult-care products including wipes, pads, containers, incontinence products, and urinary shields; clothing components; athletic and recreation products; products for applying hot or cold therapy, medical gowns (i.e., protective and/or surgical gowns), surgical drapes, caps, gloves, face masks, bandages, wound dressings, wipes, covers, containers, filters, disposable garments and bed pads, medical absorbent garments, underpads; construction and packaging supplies, industrial pads including meat pads; products for cleaning and disinfecting, wipes, covers, filters, towels, bath tissue, facial tissue, nonwoven roll goods, home-comfort products including pillows, pads, cushions, masks and body care products such as products used to cleanse or treat the skin, laboratory coats, cover-alls, and the like.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

EXAMPLES

Adhesive preparation: Sample adhesive, unless otherwise stated, was prepared by combining the components together at a temperature where the polymer was molten, and the mixture became homogeneous.

The heat of fusion (ΔHm) of the polymer was determined by DSC, in accordance with ASTM D3418-12. The DSC measurements were conducted using a TA Instruments Q2000 MDSC under the following conditions: a small sample of around 6-10 mg of the polymer was sealed in an aluminum sample pan, loaded into the instrument at room temperature and heated to 180° C. at a heating rate of 10° C./minute (first heating cycle). The sample was held for 2 minutes at this temperature to destroy its thermal history. After equilibration at this temperature for 2 minutes, the sample was cooled to −40° C. at a cooling rate of 10° C./minute. The sample was kept at −40° C. for 2 minutes and subsequently heated to 160° C. at 10° C./minute in a second heating phase (second heating cycle). All thermal effects which occurred during the three phases (e.g. glass transition, peak melting point (Tm), heat of melting (ΔHm) were subsequently evaluated by software from the experimental data files. The melting temperatures are the peak melting points from the second heat unless otherwise indicated. For polymers displaying multiple peaks, the higher melting peak temperature was reported. Areas under the curve were used to determine the heat of melting (ΔHm). The peak integration results were normalized for sample weight and reported in J/g. Melting point was measured with a differential scanning calorimetry apparatus (DSC) in accordance with ASTM 3418-12.

Viscosity was measured with a standard Brookfield viscometer (Thermosell RVT viscosimeter, available from Brookfield Engineering Laboratories, Inc., Stoughton, Mass. USA), at temperatures of 200° C. using spindle 27 in accordance with ASTM D3236.

Softening point was measured with a Ring and Ball softening point set up in accordance with ASTM E28.

The storage modulus (E') of the polymer is measured by DMA Q 800 by TA Instruments. The polymer is tested using film geometry in a torsion mode having constant 1 Hz frequency and strain within viscoelastic linear region. The temperature range starts from below 0° C. at ramp rate 5.0° C./min until the polymer melts. The temperature ramp experiment measures the viscoelastic properties in dynamic oscillatory mode. The film is cast from the melt and the final solid film has a thickness around 1 mm. Storage modulus at 25° C. and 1 Hz and 40° C. and 1 Hz are reported in Table 1.

The storage modulus (G') of the adhesive is measured by Rheometric Scientific RDA III by TA Instruments. The dynamic temperature sweep test is performed by placing an adhesive sample between two parallel plates having constant frequency 10 rad/sec and start temperature below 0° C. to until adhesive melts. Throughout the experiment the temperature increase by 5° C. in steps.

Elastic sample preparation: Elastic sample laminations were prepared by continuous elastic coating application methods known in the art. The elastic adhesive was applied with add-on levels of 25 or 35 mg/m/strand onto a LYCRA Invista 680 elastic strand with Nordson Surewrap strand applicator at a 143° C. to 155° C. using a high speed laminator at 1000 fpm with 0.1 sec open time. The elastic strand was then laminated between Clopay Breathable PE (143 or 145) substrates and NW PGI nonwoven (15 gsm) substrate with a nip roller and cooled to room temperature.

Elastic Creep Resistance Evaluation: Elastic creep resistance values were measured for initial and aged elastic samples. For the aged samples, the elastic samples were aged at 40° C. for 2 weeks and 4 weeks. The creep resistance values are listed as an average of five samples.

Creep measurement: The length of an elastic strand adhered in the stretched condition between a nonwoven sheet and a polymeric film was measured and marked ("starting length"). A sample length is stretched outside of the marked area. The elastic strands are then cut at the marked area. The amount that the filament retracts is measured following a 4 hour period at 38° C. The percent creep is then calculated in the following manner:

$$\% \text{ creep} = \frac{(\text{starting length} - \text{final length}) \times 100\%}{\text{starting length}}$$

Acceptable creep resistance of the adhesive is about 35% or less.

Table 1 sets forth certain properties of polymers used in the preparation of Examples 1 and 2 and Comparative Examples 1, 2, and 3.

"Olefin 1" is a semi-crystalline propylene co-polymer according to the description. It can be prepared according to the methods described in U.S. Publication No. 2014/0235127, the entirety of which is incorporated by reference herein.

L-MODU S-400 is a semi-crystalline propylene homopolymer according to the description. It is available from Idemitsu Kosan Co., Ltd.

REXTAC 2814 is an amorphous copolymer (propylene-butene) available from REXtac LLC.

INFUSE 9817 is an ethylene-octene olefin copolymer, available from Dow.

"Olefin 2" is a semi-crystalline propylene co-polymer. It can be prepared according to the methods described in U.S. Pat. No. 8,853,329, the entirety of which is incorporated by reference herein.

Functionalized polymer is a maleated ethylene copolymer having a melt index of 660 (g/10 min at 190° C., 2.16 Kg). The functional group, maleic anhydride, is present at about 1 wt %, based on the total weight of the functionalized polymer.

Functionalized wax is an ethylene-acrylic acid copolymer having a viscosity of 575 cP at 140° C. The functional group, acrylic acid, is present at about 5 wt % based on the total weight of the functionalized wax.

TABLE 1

| Polymer | ΔHm (J/g) | Tm (° C.) | E' @ 25° C., 1 Hz (dyn/cm$^2$) | E' @ 40° C., 1 Hz (dyn/cm$^2$) | Viscosity @ 200° C. (Pa · s) |
|---|---|---|---|---|---|
| Olefin 1 | 27 | 128 | $2.7 \times 10^9$ | $1.9 \times 10^9$ | 10 |
| Olefin 2 | 22 | 139 | $1.5 \times 10^9$ | $1 \times 10^9$ | 22.5 |
| L-MODU S-400 | 5.4 | 78 | $7.3 \times 10^8$ | $6.2 \times 10^8$ | 6.8 |
| REXTAC 2814 | n/a | n/a | $3.6 \times 10^8$ | $2.3 \times 10^8$ | 1.1 |
| INFUSE 9817 | 38 | 124 | $2.6 \times 10^8$ | $2.1 \times 10^8$ | n/a |

Examples 1 and 2, and Comparative Examples 1, 2, and 3 were prepared with the components listed in Table 2. The properties of the adhesive compositions are listed in Table 3. Henkel DISPOMELT® 897B, a rubber-based (styrene-butadiene-styrene and/or styrene-isoprene-styrene) adhesive was used as a control.

TABLE 2

| Component | Example 1 | Example 2 | Comparative Example 1 | Comparative Example 2 | Comparative Example 3 |
|---|---|---|---|---|---|
| Olefin 1 | 0 | 0 | 0 | 45 | 0 |
| Olefin 2 | 33 | 0 | 0 | 0 | 0 |
| L-MODU S-400 | 0 | 55 | 0 | 0 | 0 |
| REXTAC 2814 | 0 | 0 | 70 | 0 | 0 |
| INFUSE 9817 | 0 | 0 | 0 | 0 | 15 |

TABLE 2-continued

| Component | Example 1 | Example 2 | Comparative Example 1 | Comparative Example 2 | Comparative Example 3 |
|---|---|---|---|---|---|
| Functionalized polyolefin | 2 | 0 | 0 | 0 | 0 |
| Functionalized wax | 0 | 2 | 0 | 0 | 0 |
| Escorez 5400 | 51.5 | 0 | 0 | 43.2 | 0 |
| Eastotac H130R | 0 | 33 | 29.7 | 0 | 0 |
| Eastotac H100R | 0 | 0 | 0 | 0 | 60 |
| AC-9 | 5 | 5 | 0 | 5 | 0 |
| Epolene C10 | 0 | 0 | 0 | 0 | 14.5 |
| Indopol H300 | 3 | 4 | 0 | 0 | 0 |
| Indopol H100 | 0 | 0 | 0 | 6 | 0 |
| Calsol 5500 | 5 | 0 | 0 | 0 | 10 |
| Irganox 1010 | 0.5 | 1 | 0.3 | 0.8 | 0.5 |
| Total parts | 100 | 100 | 100 | 100 | 100 |

TABLE 3

| | Ex. 1 | Ex. 2 | Comp. Ex. 1 | Comp. Ex. 2 | Comp. Ex. 3 | Rubber (DM897B) |
|---|---|---|---|---|---|---|
| Viscosity 150° C. (cP) | 13320 | 7990 | 3500 | 6500 | 8750 | 5400 |
| Softening point (° C.) | 127 | 104.2 | 80 | 133.5 | 111 | 92 |
| Adhesive add-on: 25 mg/m/strand | | | | | | |
| Initial Creep Ave. (%) | 6.4 | 3.8 | 68.0 | 3.8 | 8.0 | 5.0 |
| Aged 2 weeks at 40° C., ave. (%) | 30.1 | 7.8 | na | 25.5 | 55.0 | 13.0 |
| Aged 4 weeks at 40° C., ave. (%) | 27.1 | 6.8 | na | 40.7 | 51.0 | 14.0 |
| Adhesive add-on: 35 mg/m/strand | | | | | | |
| Initial Creep Ave. (%) | 2.5 | 2.1 | 68.0 | 2.6 | 4 | 3.0 |
| Aged 2 weeks at 40° C, ave. (%) | 27.4 | 4.6 | na | 25.7 | 46 | 8.0 |
| Aged 4 weeks at 40° C, ave. (%) | 32.6 | 5.0 | na | 28.3 | na | 9.0 |
| Tg ° C. | 12.22 | 9.37 | −1.55 | 16.75 | 27.32 | 28.12 |
| G' 20° C., 10 rad/s (dyn/cm$^2$) | $5.37 \times 10^7$ | $1.30 \times 10^7$ | $4.08 \times 10^6$ | $1.21 \times 10^8$ | $1.40 \times 10^7$ | $1.40 \times 10^7$ |
| G' 25° C., 10 rad/s (dyn/cm$^2$) | $3.53 \times 10^7$ | $8.14 \times 10^6$ | $1.71 \times 10^6$ | $8.54 \times 10^7$ | $3.21 \times 10^6$ | $3.21 \times 10^6$ |
| G' 40° C., 10 rad/s (dyn/cm$^2$) | $1.50 \times 10^7$ | $2.71 \times 10^6$ | $6.55 \times 10^5$ | $3.23 \times 10^7$ | $3.70 \times 10^5$ | $3.70 \times 10^5$ |
| ΔHm (J/g) | 5.7 | 5.6 | na | 24 | 5.0 | na |
| Tm (° C.) | 134 | 99 | na | 126 | 114 | na |

Example 1 describes an adhesive where a semi-crystalline polypropylene copolymer of the disclosure is used for an elastic application. The semi-crystalline polypropylene copolymer has the material properties such as storage modulus (E') at 40° C. and 1 Hz, viscosity, and crystallinity to provide the necessary stiffness or cohesive strength to maintain initial and aged creep performance. Example 1 provides an adhesive with balanced material properties, for example storage modulus (G') at 40° C. and 10 rad/s and processing viscosity.

Example 2 describes an adhesive where a semi-crystalline polypropylene homopolymer is used for an elastic application. The semi-crystalline polypropylene homopolymer, L-MODU, has the material properties such as storage modulus (E') at 40° C. and 1 Hz, viscosity, and crystallinity to provide the stiffness or cohesive strength to maintain the initial and aged creep performance. Example 2 provides an adhesive with balanced material properties, for example storage modulus (G') at 40° C. and 10 rad/s and processing viscosity.

Comparative Example 1 describes an adhesive where an amorphous poly-a-olefin (APAO) is used as the main polymer for an elastic application. The lack of crystallinity and the low storage modulus (E') at 40° C. and 1 Hz for the APAO do not provide the stiffness to maintain even the initial creep performance.

Comparative Example 2 describes an adhesive where a semi-crystalline polypropylene copolymer is used for an elastic application. The semi-crystalline polypropylene copolymer, olefin 1, has an appropriate viscosity for processing and application of the adhesive, however, even though its storage modulus (E') at 40° C. and 1 Hz and crystallinity provide stiffness or cohesive strength to maintain the initial creep performance, the aged creep performance is compromised. The formulation is balanced in such a way to provide an adhesive with the right processing viscosity but the storage modulus (G') at 40° C. and 10 rad/s appears to be too high, yielding an adhesive too stiff to maintain the creep performance under aging.

Comparative Example 3 describes an adhesive where an ethylene-octene olefin copolymer is used for an elastic application. The ethylene-octene olefin polymer, INFUSE 9817, does not have high enough storage modulus (E') at 40° C. and 1 Hz to provide the necessary stiffness or cohesive strength to maintain the aged creep performance which is then compromised. The formulation is balanced in such a way to provide an adhesive with the right processing viscosity but the storage modulus (G') at 40° C. and 10 rad/s is too low to maintain the creep performance after aging.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed:

1. An article comprising:
    a nonwoven substrate;
    an elastic strand or an elastic film; and
    a stretch adhesive composition consisting of:
        (i) about 25 wt. % to about 65 wt. % of a single semi-crystalline propylene co-polymer characterized by
            a heat of fusion ($\Delta Hm$) is between 20 J/g and 24 J/g;
            a DSC melting temperature of 125° C. to 165° C., measured in accordance with ASTM 3418-12;
            a storage modulus (E') at 40° C. and 1 Hz of between about $3.0 \times 10^8$ dyn/cm$^2$ and about $1.7 \times 10^9$ dyn/cm$^2$; and
            a viscosity ($\eta$) at 200° C. of between about 2 Pa·s and about 100 Pa·s,
        (ii) about 1 wt. % to about 5 wt. % of an adhesion promoter that is a functionalized polyethylene, functionalized tackifier, functionalized plasticizer, or a mixture thereof;
        (iii) about 10 wt. % to about 55 wt. % of a tackifier; and
        (iv) optionally, up to 8 wt. % of a plasticizer; up to 2 wt % of an antioxidant, stabilizer, crosslinking agent, filler, colorant, rheology modifier, or a mixture thereof; and up to 10 wt % of a non-functionalized wax;
    wherein the stretch adhesive composition exhibits creep resistance of about 35% or less for both an initial creep resistance and an aged creep resistance measured after about 28 days at about 40° C.; and
    wherein the wt % is based on the weight of the stretch adhesive composition.

2. The article of claim 1, wherein the storage modulus at 40° C. and 1 Hz of the semi-crystalline propylene polymer is between about $5.0 \times 10^8$ dyn/cm$^2$ and about $1.1 \times 10^9$ dyn/cm$^2$.

3. The article of claim 1, wherein the viscosity of the semi-crystalline propylene polymer at 200° C. is between 20 Pa·s and 24 Pa·s.

4. The article of claim 1, wherein the adhesion promoter is a functionalized polyethylene.

5. The article of claim 1, wherein the stretch adhesive composition has a viscosity at 150° C. of between about 7,500 cPs and about 15,000 cPs.

6. The article of claim 1 that is a diaper, sanitary napkin, pet sheet, hospital gown, or surgical garment.

7. The article of claim 6 further comprising a substrate that is tissue, cotton, nonwoven fabric, or polyolefin film.

* * * * *